United States Patent
Beloussov et al.

(10) Patent No.: US 7,368,740 B2
(45) Date of Patent: *May 6, 2008

(54) CONFIGURATION MANAGEMENT AND RETRIEVAL SYSTEM FOR PROTON BEAM THERAPY SYSTEM

(75) Inventors: Alexandre V. Beloussov, San Bernardino, CA (US); Michael A. Baumann, Riverside, CA (US); Howard B. Olsen, Irvine, CA (US); Dana Salem, Riverside, CA (US)

(73) Assignee: Loma Linda University Medical Center, Loma Linda, CA (US)

( * ) Notice: Subject to any disclaimer, the term of this patent is extended or adjusted under 35 U.S.C. 154(b) by 0 days.

This patent is subject to a terminal disclaimer.

(21) Appl. No.: 11/460,880

(22) Filed: Jul. 28, 2006

(65) Prior Publication Data

US 2007/0018120 A1 Jan. 25, 2007

Related U.S. Application Data

(63) Continuation of application No. 10/994,911, filed on Nov. 22, 2004, now Pat. No. 7,084,410, which is a continuation of application No. 10/744,697, filed on Dec. 22, 2003, now Pat. No. 6,822,244.

(60) Provisional application No. 60/438,281, filed on Jan. 2, 2003.

(51) Int. Cl.
*G21G 4/00* (2006.01)

(52) U.S. Cl. .............................. 250/492.3; 250/492.1; 250/492; 378/207; 378/65; 702/183

(58) Field of Classification Search .................... None
See application file for complete search history.

(56) References Cited

U.S. PATENT DOCUMENTS

| 4,870,287 A | 9/1989 | Cole et al. |
| 5,260,581 A | 11/1993 | Lesyna et al. |

(Continued)

FOREIGN PATENT DOCUMENTS

WO   WO 02/45793 A2   6/2002

OTHER PUBLICATIONS

Jun Matsu'ura, "Systems for Overall Control and Beam Transport of the HIMAC," Mitsubishi Electric Advance, Mitsubishi Electric Corporation, Tokyo, JP, vol. 72, Sep. 1995 pp. 5-7.

(Continued)

*Primary Examiner*—Jack I. Berman
*Assistant Examiner*—Zia R. Hashmi
(74) *Attorney, Agent, or Firm*—Knobbe, Martens, Olson & Bear, LLP

(57) ABSTRACT

In a complex, multi-processor software controlled system, such as proton beam therapy system (PBTS), it may be important to provide treatment configurable parameters that are easily modified by an authorized user to prepare the software controlled systems for various modes of operation. This particular invention relates to a configuration management system for the PBTS that utilizes a database to maintain data and configuration parameters and also to generate and distribute system control files that can be used by the PBTS for treatment delivery. The use of system control files reduces the adverse effects of single point failures in the database by allowing the PBTS to function independently from the database. The PBTS accesses the data, parameters, and control settings from the database through the system control files, which insures that the data and configuration parameters are accessible when and if single point failures occur with respect to the database.

23 Claims, 9 Drawing Sheets

U.S. PATENT DOCUMENTS

| | | |
|---|---|---|
| 5,511,549 A | 4/1996 | Legg et al. |
| 5,845,276 A | 12/1998 | Emerson et al. |
| 5,895,926 A | 4/1999 | Britton et al. |
| 6,023,694 A | 2/2000 | Kouchi et al. |
| 6,026,392 A | 2/2000 | Kouchi et al. |
| 6,178,430 B1 | 1/2001 | Cohen et al. |
| 6,182,060 B1 | 1/2001 | Hedgcock et al. |
| 6,200,025 B1 | 3/2001 | Rich |
| 6,822,244 B2 | 11/2004 | Beloussov et al. |
| 7,084,410 B2 * | 8/2006 | Beloussov et al. ....... 250/492.1 |
| 2004/0164254 A1 | 8/2004 | Beloussov et al. |
| 2005/0072940 A1 | 4/2005 | Beloussov et al. |

OTHER PUBLICATIONS

Notice of Allowance of Mar. 22, 2006 for U.S. Appl. No. 10/994,911.

Terminal Disclaimer and Response to Office Action of Aug. 30, 2007 for U.S. Appl. No. 10/994,911.

Office Action of Aug. 30, 2007 for U.S. Appl. No. 10/994,911.

Notice of Allowance of Aug. 13, 2004 for U.S. Appl. No. 10/744,697.

* cited by examiner

CONFIGURATION MANAGEMENT AND RETRIEVAL SYSTEM FOR PROTON BEAM THERAPY SYSTEM

RELATED APPLICATIONS AND CLAIM OF PRIORITY

This application is a continuation of U.S. patent application Ser. No. 10/994,911 filed Nov. 22, 2004, now U.S. Pat. No. 7,084,410, and titled "CONFIGURATION MANAGEMENT AND RETRIEVAL SYSTEM FOR PROTON BEAM THERAPY SYSTEM, which is also a continuation of U.S. patent application Ser. No. 10/744,697 filed Dec. 22, 2003, now U.S. Pat. No. 6,882,244, and titled "CONFIGURATION MANAGEMENT AND RETRIEVAL SYSTEM FOR PROTON BEAM THERAPY SYSTEM," and claims the benefit of U.S. Provisional Application No. 60/438,281 filed Jan. 2, 2003.

BACKGROUND OF THE INVENTION

1. Field of the Invention

The present invention relates to particle radiation therapy systems and, in particular, concerns an improved data storage system that reduces the effects of single point failures for radiation beam therapy systems.

2. Description of the Related Art

Particle radiation therapy involves coordinating complex systems and devices to enable targeting of specific cancerous regions of a patient. In particular, proton beam therapy utilizes one or more precisely aligned particle streams to irradiate cancer or tumor cells. The energized protons disrupt targeted cells or tissue so as to effectively halt the progression of the disease. In proton beam therapy, the patient should be accurately positioned with respect to the one or more beams so that the stream irradiates only the desired target region. Otherwise, the stream may damage other healthy cells within the patient's body. Specific alignment in this manner requires numerous control systems to maintain accurate and precise dosage delivery to a plurality of patients during prescribed treatments.

As described in U.S. Pat. No. 4,870,287, a proton treatment facility may comprise a proton energy source, an injector, an accelerator, a beam transport system, a switchyard, and a plurality of treatment stations so as to accommodate multiple patients. Each treatment station may comprise a plurality of treatment components such as treatment platforms, gantry structures, and patient monitoring components. Additionally, control and monitoring of the proton treatment facility may be directed by computer and hardware subsystems, which coordinate the activities of each treatment station using software configurable components.

Moreover, control system activities may include beam intensity management, beam position orientation and modification, digital imaging performance, safety condition monitoring, and various other treatment functions. Together these systems form a highly complex collection of hardware and software components. The complexity of the proton treatment facility may be further magnified by managing multiple treatment stations where additional requirements for system redundancy and selective control of each treatment station is required.

The complex architecture of proton therapy systems present numerous obstacles for coordinating control of a high volume patient throughput. On a typical treatment day, prescribed treatment dosages may be configured for many patients using a plurality of treatment stations, whereby delivery of simultaneous treatments may effect concurrent treatment dosages between patients. For example, each treatment station may require a different proton beam energy delivery, wherein the overall energy is calculated and produced at the source, the switchyard diverts the proper amount of proton beam energy to each treatment station, and the multiple gantries are positioned to deliver the diverted energy to the target regions of the patients on the treatment platforms.

To elicit the coordination control of multiple treatment stations, conventional proton beam therapy control systems use either a centralized computer system, such as a database server, or separate computer subsystems to localize control. The problem with a centralized computer system is that, if one or more treatment components fails to function or goes offline, the system as a whole may shut down. Also, if the centralized computer fails, the treatment components may stop functioning because they rely on the centralized computer for operational instructions. Unfortunately, with the high volume of treatments to be delivered, a system shut down would be inconvenient, costly, and reduce treatment efficiency.

Some treatments may be delayed or postponed for another day, which inconveniences everyone including the patient and the system operators. In other circumstances, a delayed or postponed treatment may degrade the therapy provided, wherein the treatment time may need to be reduced or the dosage modified to accommodate a larger number of treatments in a reduced period of time. Additionally, delayed treatments may also incur additional treatment costs due to extended periods of operation, where system operators are paid overtime wages and the treatment delivery systems remain operable for longer periods of time. Therefore, a centralized computer alone is not the answer due to unavoidable failures that may occur during treatment delivery, which may endanger some patients.

Since patient safety is a great concern, some conventional proton beam therapy control systems use separate computer subsystems to localize control to particular treatment components. The problem with localized control is that each component requires a system operator to manually enter prescribed treatment and operational parameters for each patient at each treatment station. Unfortunately, the length of each treatment would be extended due to the additional time needed to enter prescribed parameters for each patient treatment and system operation. Also, the high volume of treatments to be delivered would need to be reduced to accommodate the additional time or additional system operators would need to be hired to extend the treatment day, which results in additional operational costs.

Hence, there is a need for an improved proton beam therapy control system that manages multiple treatment delivery components and coordinates delivery of simultaneous treatments without compromising patient safety. There is also a need for an improved proton beam therapy control system that reduces the adverse effects of centralized computer failures if one or more treatment components fails to function. Additionally, this system architecture should be able to accommodate the complexity associated with proton beam therapy control systems while maintaining an acceptable level of user interactive simplicity so as to facilitate configuration, maintenance, and development in an efficient manner.

SUMMARY OF THE INVENTION

The aforementioned needs are satisfied by a radiation beam therapy system having a plurality of treatment devices including a radiation beam source and a beam transport device. In one embodiment, the radiation beam therapy system comprises a database component that stores subsets of parameters associated with selected treatment devices, wherein the parameters comprise instructional information that can be used to configure the selected treatment devices for operation. In addition, the radiation beam therapy system comprises an interface component that allows a user to modify the subsets of parameters associated with selected treatment devices stored in the database. Moreover, the radiation beam therapy system comprises a management component that extracts subsets of parameters from the database and generates data storage elements comprising the extracted subsets of parameters in a format recognizable by the selected treatment devices, wherein the data storage elements permit configuration of the selected treatment devices based, at least in part, on the instructional information comprised therein, the management component further distributes the data storage elements to the selected treatment devices to thereby permit the selected treatment devices to operate independently of the database component.

In one aspect, operation of the selected treatment devices includes a treatment mode of operation. The plurality of treatment devices includes at least one of a charged particle source, an accelerator, and a beam transport system. The source or accelerator includes a proton synchrotron and the beam transport system includes a plurality of steering and focussing magnets with beam sensors distributed along an evacuated beam transport tube. The beam transport system connects to a series of switchyards that include an array of dipole bending magnets which deflect the beam to any one of a plurality of beam focussing and deflection optics leading to respective treatment locations having rotatable gantries. Also, a beam delivery system may be located within each rotatable gantry, which may be adapted to deliver therapeutic radiation doses to a patient lying on a treatment platform according to a specific patient treatment plan.

In another aspect, the subsets of parameters include treatment data, configuration parameters, operational parameters, and control settings for the selected treatment devices. The selected treatment devices are software controlled instruments that require at least one of the subsets of parameters for operation and treatment. The database component comprises a centralized database server, which stores configuration and operational information, such as data, parameters, and control settings, for the selected treatment devices in a manner so as to provide easy access to the stored configuration and operational information, wherein parameter retrieval and modification are easily performed by the centralized database server via requests from the interface component. The centralized database server provides configuration management activities, which may include record keeping and version/revision control. The management component reduces the occurrence of single point failures by generating appropriate data storage elements and distributing the data storage elements to the selected treatment devices. The distribution of data storage elements by the management component affords the selected treatment devices operational independence from the database component due to the associated reliance on the data storage elements for parameter retrieval and operational configuration.

In still another aspect, the radiation beam therapy system comprises at least one communication link between the management component and the selected treatment devices so as to distribute the generated data storage elements to the selected treatment devices. The subsets of parameters are stored in the database component in at least one of database table structures, records, and values. The data storage elements are arranged in a consolidated information set that is recognizable by the selected treatment devices. The consolidated information set exploits the native functionality of the selected treatment devices in a manner such that an additional numerical or supplemental program or application may be unnecessary for the selected treatment devices to recognize the configuration parameter values from the data storage elements. The data storage elements comprise a data type that is stored and accessed in a file-oriented manner as is suitable for each selected treatment devices. The data storage elements comprise a data type that is stored and accessed in an address-oriented manner as is suitable for each selected treatment devices. The data storage elements comprise one or more volatile or non-volatile system control files. The data storage elements comprise one or more system control files including flat files. The one or more system control files include one or more flat files.

In still another aspect, the management component sends configurable parameters to each treatment device, and wherein a selected treatment device retrieves usable parameters from the configurable parameters. Additionally, the management component selectively sends configurable parameters to each treatment device representing usable parameters by each treatment device.

The aforementioned needs are also satisfied by a radiation beam therapy system comprising a plurality of distributed functional components whose operation is coordinated to elicit a selected operational mode. In one embodiment, the system comprises a database component that stores a plurality of parameters associated with the distributed functional components. In addition, the system comprises an interface component that allows a user to select an operational mode for which the database component identifies appropriate subsets of parameters that are associated with the distributed functional components and generates at least one system control file containing an appropriate subset of parameters used to configure a selected distributed functional component to operate in such a manner to elicit the selected operational mode. Moreover, the system comprises a control file distribution component that provides each of the distributed functional components with the appropriate system control file such that the functional components are able to operate substantially independently of the database component while eliciting the selected operational mode.

The aforementioned needs are also satisfied by a radiation beam therapy system comprising, in one embodiment, a plurality of treatment devices including a radiation beam source and a beam transport device and a database that stores subsets of specific parameters associated with selected treatment devices, wherein the specific parameters comprise a logical collection of instructional information that can be used to configure the selected treatment devices for operation. In addition, the system comprises an interface that allows a user to modify the subsets of specific parameters associated with selected treatment devices stored in the database. Moreover, the system comprises a management component that extracts selected subsets of specific parameters from the database and generates system control files comprising the extracted subsets of specific parameters in a format recognizable by the selected treatment devices, wherein the system control files permit configuration of the selected treatment devices based, at least in part, on the instructional information comprised therein, the management component further distributes the system control files to the selected treatment devices to thereby permit the selected treatment devices to operate independently of the database. Furthermore, the subsets of specific parameters comprise, for example, subsets of instrument specific parameters.

The aforementioned needs are also satisfied by a radiation beam therapy system having a plurality of functional components including a radiation beam source and a beam transport device. In one embodiment, the system comprises a database that stores subsets of configurable parameters associated with the operation of the functional components, the database further comprising an interface component that allows a user to modify the stored subsets of configurable parameters. In addition, the system comprises a management component that retrieves subsets of configurable parameters associated with selected functional components from the database, the management component further generating control files from the stored configurable parameters, and subsequently distributing the generated control files to the identified functional components such that the identified functional components can operate independently.

The aforementioned needs are also satisfied by a radiation beam therapy system comprising, in one embodiment, at least one functional component that can be configured for treatment delivery via a subset of configurable parameters and a database component that stores the subset of configurable parameters as a logical collection of information, the database component having a user interface that allows a user to modify the logical collection of information. In addition, the system comprises a management component that communicates with the database component and the at least one functional component, wherein the management component identifies the subset of configurable parameters associated with the at least one functional component, generates a first file from the identified subset of configurable parameters, and distributes the first file to the at least one functional component so that, upon reception of the first file, the at least one functional component can extract the subset of configurable parameters from the first file and configure itself for treatment delivery.

The aforementioned needs are also satisfied by a method for managing a plurality of distributed instruments used in treatment delivery for a radiation beam therapy system. In one embodiment, the method comprises storing operational instructions for each instrument within a centralized configuration management system having a database component in which the operational instructions are maintained and selecting an operational mode for the radiation beam therapy system and identifying a subset of operational instructions stored in the database component for each of the distributed instruments to be used in configuring the radiation beam therapy system to function in the selected operational mode. In addition, the method comprises generating a data storage element for each of the distributed instruments containing the required operational instructions necessary to configure each distributed instrument to function in such a manner so as to result in the radiation beam therapy system functioning in the selected operational mode. Moreover, the method comprises transferring the data storage element to the distributed instruments thereby providing the necessary operational instructions for a selected distributed instrument to operate without requiring further access to the centralized configuration management system to elicit functioning of the radiation beam therapy system in the desired operational mode.

In one aspect, generating a data storage element includes generating a plurality of data storage elements. Also, generating a data storage element includes generating at least one flash memory element. Additionally, generating a data storage element includes generating at least one system control file. Moreover, transferring the data storage element to the distributed instruments includes transmitting the data storage element to the distributed instruments.

The aforementioned needs are also satisfied by a method of configuring a radiation beam therapy system having a plurality of functional components for directing a beam to at least one of a plurality of treatment locations. In one embodiment, the method comprises maintaining a plurality of configurable parameters in a database, the configurable parameters used to coordinate the function of the plurality of functional components thereby eliciting operational control of the radiation beam therapy system and selecting an operational mode in which the beam is to be directed to a particular treatment location with a desired set of operational parameters. In addition, the method comprises identifying subsets of parameters from the plurality of configurable parameters maintained in the database that are used to configure and control the functional components in such a manner so as to direct the beam to the selected treatment location with the desired set of operational parameters. Moreover, the method comprises generating at least one system control file which reflects the subsets of parameters used to configure and control the functional components and distributing the at least one system control file to at least one of the plurality of functional components thereby directing the operation of the functional components.

These and other objects and advantages of the present invention will become more apparent from the following description taken in conjunction with the accompanying drawings.

DETAILED DESCRIPTION OF THE PREFERRED EMBODIMENT

Figure 1:
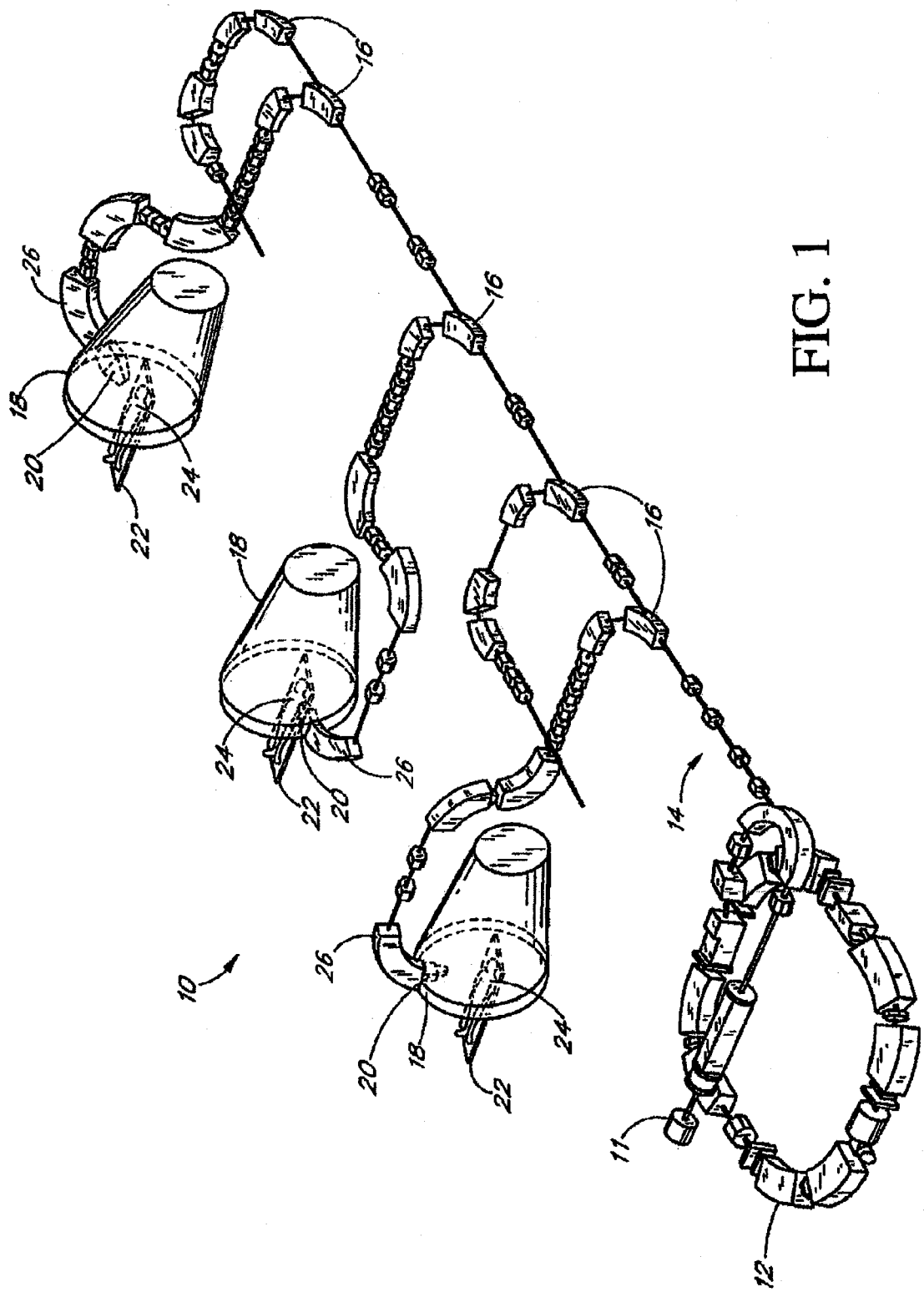
FIG. 1 illustrates one embodiment of a clinically-based radiation beam therapy system, such as, for example, a proton beam therapy system (PBTS), that may used in a particle radiation treatment facility.

In complex, multi-processor software controlled systems, it may be important to provide treatment configurable parameters that are easily modified by an authorized user to prepare the software controlled system for various modes of operation. In one embodiment, a configuration management system of the present invention provides a centralized database server, which stores configuration and operational information, such as data, parameters, and control settings, for the software controlled systems. Advantageously, the database approach provides easy access to the stored configuration and operational information, wherein parameter retrieval and modification are easily performed by the configuration management system via requests from a user interface system. Additionally, the configuration management system provides configuration management activities, which may include record keeping and version/revision control as will be described in greater detail herein below.

In conventional treatment delivery systems, the treatment delivery components access operational and configuration parameters directly from the database component using a single point acquisition approach. Single point acquisition requires a direct dependence on the database component for operation and parameter retrieval via a direct communication link between the treatment delivery devices and the database component. As a result of operational dependence, if a network problem occurs and the database component is offline or unavailable, then the conventional treatment delivery systems are forced to shut down and patient treatments may be terminated until the database component is functionally online or available. Single point failures are disadvantageous to patient health, treatment stability, and operational efficiency.

Conversely, the present invention reduces the occurrence of single point failures by generating a static document, such as a flat text file, read-only file, or flash memory element, comprising operational and configuration parameters and distributing the static document to the treatment delivery components. The distribution of static documents affords the treatment delivery components operational independence from the database component due to the associated reliance on the static documents for parameter retrieval and operational configuration. Although a communication link may be used to distribute the generated static document or system control file to the treatment delivery components, operational reliance is advantageously shifted to the static document. The scope and functionality of the static documents or system control files will be described in greater detail herein below.

Moreover, for ease of updating and retrieval, configuration parameters, for example, may be stored in the database table structures as records or values. When generating the static document or system control file, the retrieved configuration parameter values may be arranged in a consolidated information set that is recognizable by the treatment delivery components. Advantageously, the consolidated information set exploits the native functionality of the treatment delivery devices in a manner such that an additional numerical or supplemental program or application may be unnecessary for the treatment delivery devices to parse the configuration parameter values from the static document. Moreover, the static documents or system control files provide fast, localized parameter retrieval capability and independent operational capabilities for the software controlled systems as will be further described in greater detail herein below.

Reference will now be made to the drawings wherein like numerals refer to like parts throughout. FIG. 1 illustrates one embodiment of a clinically-based radiation beam therapy system, such as, for example, a proton beam therapy system (PBTS) 10, that may be used in a particle radiation treatment facility. In one embodiment, the proton beam therapy system 10 may comprise a plurality of treatment delivery components including a charged particle source 11, an accelerator 12, and a beam transport system 14. Additionally, the source/accelerator 11, 12 may comprise, for example, a proton synchrotron and the beam transport system 14 may comprise, for example, a plurality of steering and focussing magnets with beam sensors distributed along an evacuated beam transport tube.

In one aspect, the beam transport system 14 connects to a series of switchyards 16 that may comprise an array of dipole bending magnets which deflect the beam to any one of a plurality of beam focussing and deflection optics 26 leading to respective treatment locations having rotatable gantries 18. Moreover, a beam delivery system 20 may be located within each rotatable gantry 18, which may be adapted to deliver therapeutic radiation doses to a patient 24 lying on a treatment platform 22, according to a specific patient treatment plan. An exemplary proton beam treatment system is more fully disclosed in U.S. Pat. No. 4,870,287, which is hereby incorporated by reference in its entirety.

In operation, charged particle beams of a predefined energy may be generated by the proton synchrotron 12 and transported by the beam transport system 14 to the switchyards 16. The switchyards 16 may be configured to select a one or more gantries 18 for transport of radiation thereto. Each rotatable gantry 18 is capable of orienting the beam delivery system 20 relative to the target location of the patient 24. Beam orientation allows directed deposition of radiation to a predefined location along the rotation axis or a so-called isocenter. Additionally, to facilitate accurate and precise dosage delivery to one or more of the patients 24, the beam delivery system 20 may be positioned, configured, and calibrated for radiation delivery according to prescribed specifications of the patient treatment plan.

One of the central components of the proton beam therapy system 110 is the radiation delivery system 20, designed to deliver precise dose distributions to a target volume within a patient. In general, such delivery systems are comprised of components which may either modify or monitor specific properties of a radiation beam relevant to the treatment plan. The beam delivery system 20 may, for example, comprise a device to spread or otherwise modify the beam position and profile, a dispersive element to modify the beam energy and a plurality of beam sensors to monitor such properties. Additional disclosure relating to the radiation delivery system 20 is provided in U.S. Pat. No. 4,870,287.

Figure 2:
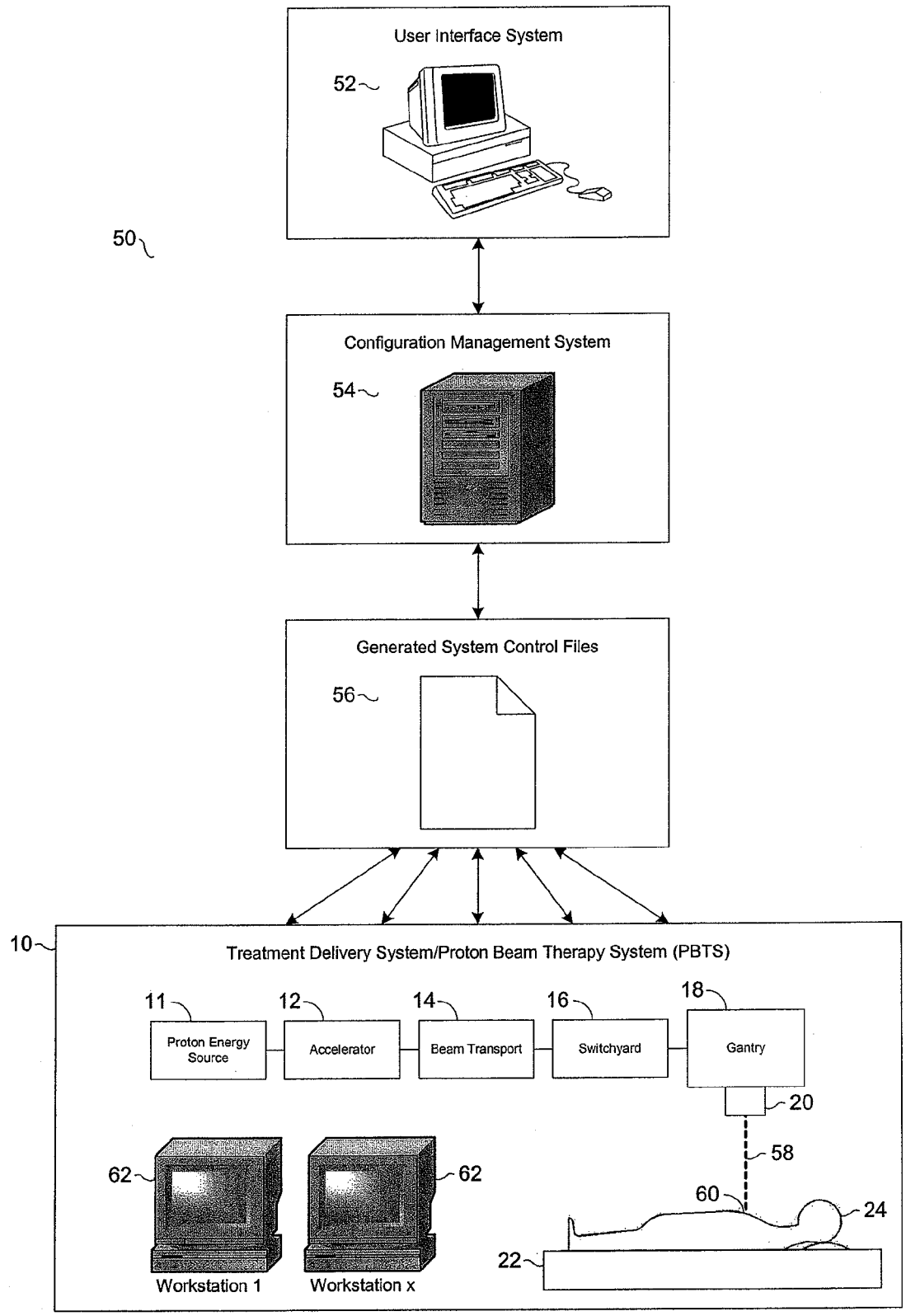
FIG. 2 illustrates one embodiment of a PBTS configuration management system that may be used for accessing and maintaining PBTS configuration data and parameters.

FIG. 2 illustrates one embodiment of a central configuration of a particle radiation treatment facility 50 that may be used to provide proton beam therapy treatments to patients in a manner as previously described with reference to FIG. 1. The particle radiation treatment facility 50 may comprise the proton beam therapy system (PBTS) 10 of FIG. 1, a user interface system 52, and a configuration management system 54 that may be used to generate one or more static documents or system control files 56 for the PBTS treatment delivery components 11, 12, 14, 16, 18, 20 of the PBTS 10. In addition, the one or more generated system control files 56 may be distributed to the PBTS 10 by the configuration management system 54 in a manner so as to provide configuration data and parameters in a recognizable format to the PBTS treatment delivery components 11, 12, 14, 16, 18, 20.

In one embodiment, the user interface system 52 may comprise a generally known computer workstation, such as a personal computer, that may be used to retrieve and modify the configuration parameters for the PBTS 10. One or more users, such as system operators, field service engineers, medical physics personnel, facility administrators, etc., may update PBTS configuration data, parameters, and/or control settings in the configuration management system 54 via the user interface system 52. The user interface system 52 provides access to data, parameters, and control settings that may be used to configure the previously mentioned PBTS treatment delivery components in the PBTS 10. The PBTS 10 may be given access to the configuration data through the system control files 56 that may be generated and provided by the configuration management system 54.

It should be appreciated that there may be more than one user interface system 52 to the configuration management system 54 without departing from the scope of the present teachings. However, for safety reasons, a preferred embodiment may comprise one designated user interface system 52 to the configuration management system 54 to update configuration data, parameters, and control settings for the PBTS treatment delivery components 11, 12, 14, 16, 18, 20 in the PBTS 10. It should be appreciated that there are configurable parameters and control settings that may apply to software related components as well as the hardware related components. Some software and hardware components that may be configured through the configuration management system 54 may include, but are not limited to, power supplies, tesla meters, sensors, detectors, timing control systems, user interfaces, network configurations, and safety systems.

In one embodiment, the configuration management system 54 may comprise a generally known centralized computer system, such as a database server, that may be used to store the PBTS configuration data and parameters in database components, such as files, in a manner so as to be easily retrievable by the user interface system 52 when prompted by a user. Advantageously, the manipulation of the configuration data and parameters through the configuration management system 54 allows for maintaining configuration data and parameter integrity as well as providing an interactive interface to the user. In a manner as will be described in greater detail herein below, the configuration management system 54 may comprise processing and management components that may be used to verify updated parameter settings to an acceptable operational range. For example, if the operational range of a power supply is between 0 and 500 amps, then the management component verifies that supply output is not set less than 0 amps and greater than 500 amps.

In one embodiment, the configuration management system 54 uses a PBTS software application that allows authorized users to easily access and modify the PBTS configurable parameters while maintaining data integrity. The PBTS software application may be used in conjunction with common desktop environments on various platforms, such as those used with Solaris™ and X Windows™ on UNIX based platforms. In one aspect, a configurable parameter may comprise a piece of data or information needed by the PBTS 10 to configure, for example, control settings, wherein the value of the configurable parameter may vary depending on the treatment dosage and/or environment. Some of the devices in the PBTS 10 need configuration data for proper initialization. For example, magnets are configured with default output specific to their target energy. Moreover, other functional components of the PBTS 10, such as ion source, power supplies, timing, etc., may require configurable initialization data, scale factors, conversion factors, mapping, etc.

As will be described in greater detail herein below, the data is accessible to the user through a graphical user interface (GUI) via the user interface system 52, and the data is stored and maintained in a database component of the configuration management system 54. When an authorized user requests a configuration update, a connection to the database component is established and any modifications to the data are applied to the database component. In addition, authorized user accounts may be created via the user interface system 52, wherein authorized users comprises varying degrees of permission or access levels, which may be determined by administrators. For example, different types of users may be granted access to data related only to a specific job function. Accelerator staff may be allowed to modify accelerator related parameters, such as magnet settings. Medical physicians may be allowed to modify treatment room related parameters, such as detectors and scattering foils. Various other users, such as field service personnel and system administrators may have access to data needed to maintain the system.

Moreover, the database component of the PBTS configuration management component 54 may be initialized with two sets of data: treatment data and non-treatment data. The treatment set may comprise configuration data that has been approved for treatment operations. In most cases, there is one treatment set or one set of approved treatment data that is available. The non-treatment set may comprise configuration data that may be used for other functional operations, such as research, maintenance, and/or tuning. For the most part, authorized users are able to retrieve and view most configurable parameters. If a user has write access to a parameter, then the user is able to modify its value within an acceptable range, which will be described in greater detail herein below. However, proposed modifications related to treatment data is subject to approval by a designated administrator, wherein the designated administrator is responsible for patient treatment and approving proposed modifications to the treatment data.

In one embodiment, the PBTS 10 of FIG. 1 may further comprise one or more PBTS workstations 62 that may house the hardware and software used to operate and control the PBTS treatment delivery components 11, 12, 14, 16, 18, 20 of the PBTS 10. The PBTS workstations 62 function independently from the configuration management system 54 so as to provide localized control to the PBTS 10. As previously mentioned, the user interface system 52 is used to interact with the configuration management system 54. Conversely, the PBTS workstations 62 are used to interact with the PBTS treatment delivery components 11, 12, 14, 16, 18, 20. In one embodiment, there is no direct link between the configuration management system 54 and the PBTS 10. Instead, the PBTS workstations 62 and/or the PBTS 10 access the PBTS configuration data, parameters, and control settings from the configuration management system 54 via the system control files 56.

In one aspect, it should be appreciated by those skilled in the art that the configuration management system 54 provides one or more system control files 56 to the treatment delivery components 11, 12, 14, 16, 18, 20 of the treatment delivery system 10. Additionally, it should also be appreciated that the treatment delivery components 11, 12, 14, 16, 18, 20 may retrieve one or more operational parameters from the system control files 56. In another aspect, it should be appreciated by those skilled in the art that the management component is adapted to send configurable parameters to each treatment device, wherein a selected treatment device retrieves usable parameters from the configurable parameters. Moreover, the management component is further adapted to selectively send configurable parameters to each treatment device representing usable parameters by each treatment device.

Advantageously, this particular embodiment provides a separation of control between the configuration management system 54 and the PBTS workstations 62. Configuration data, parameters, and control settings are more easily updated using the configuration management system 54, which offers more reliable database management and controlled parameter revision. The generation of system control files 56 allows the PBTS workstations 62 to access the PBTS configuration data, parameters, and control settings when and if the configuration management system 54 is offline or unavailable. Therefore, the PBTS 10 is able to operate independently of the configuration management system 54.

During treatment delivery, the operation of the PBTS treatment delivery components 11, 12, 14, 16, 18, 20 are desirably coordinated to direct a precisely calibrated and aligned proton beam 58 towards a specific target region or isocenter 60 of the patient 24. As previously described, the patient 24 is supported by the treatment platform 22 and the gantry 18 is rotatable about an axis of rotation and is used to properly align the proton beam 58 with respect to the patient 24 and the isocenter 60. The PBTS control system 62 monitors and coordinates the operational activities of the hardware and software subsystems used to configure and direct the proton beam 58 as well as insure patient safety. Patient safety is a primary concern in radiation treatment and strict control over the PBTS 10 must be maintained at all times to insure that the proton beam 58 is accurately and precisely directed with an appropriate intensity or energy level. It should be appreciated that a more in depth discussion relating to the PBTS control system 62 is more fully disclosed in U.S. Pat. No. 5,260,581, which is hereby incorporated by reference in its entirety.

In addition, the PBTS 10 including the PBTS workstations 62 may utilize the system control files 56 to access configuration data, parameters, and control settings from the configuration management system 54. In one embodiment, the system control files 56 may comprise a series of strings or characters in one or more recognizable files or formats that may be parsed by the PBTS 10, PBTS workstations 62, or the functional components 11, 12, 14, 18, 20 of the PBTS 10 to retrieve configuration data, parameters, etc. stored in a control file format, such as, for example, a flat file, binary file, flash memory file, etc. One advantage to using flat files is that flat files are human readable, but various other file structures, such as binary files, may be used by those skilled in the art without departing from the scope or functionality of the present teachings. Moreover, in one aspect, the system control files 56 may be delineated using a reference identifier, such as a comma, hyphen, semi-colon, etc. Alternatively, strings may be delineated using codes that signify tabs or new lines. Additionally, a sequentially oriented group of characters that are not likely to be found in the record itself may serve as the reference identifier for string parsing.

In various embodiments, system control files 56 may be file and/or address oriented and stored in a variety of different formats. For example, a file-oriented schema may comprise a "textual document" (e.g. based on the ASCII character set) which is stored and accessed as a discrete file using a non-volatile data storage device (e.g. a hard disk drive, optical drive, tape drive, flash memory device, etc.). Likewise, an address-oriented schema may comprise system control file information stored in a manner that may be accessible at selected locations within a volatile or non-volatile memory or storage device (e.g. bits/bytes of information stored at a particular memory address). It will further be appreciated that the information contained in the system control file may be represented in numerous different manners, such as for example, using binary, octal, hexadecimal, html or other data types/representations. These data types may be stored and accessed in file-oriented, address-oriented, or other organizational manners as is suitable for each instrument or device which is desirably configured to use the system control file information.

In certain embodiments, the system control files 56 may comprise, for example, data files or formats stored in various types of data storage elements, such as flash memory, read-only memory, etc. As is generally known, programmable read-only memory (PROM) is read-only memory (ROM) that can be modified once by a user. Since PROM processes are relatively inflexible, many PROM chips designed to be modified by users may be implemented with erasable programmable read-only memory (EPROM) or electrically erasable programmable read-only memory (EEPROM), which can be programmed, erased and reprogrammed multiple times. In addition, flash memory represents a type of non-volatile memory that can be erased and reprogrammed in units of memory blocks. Other types of devices that may be used in accordance with the present teachings may include magnetic and optical data storage formats, such as compact disks, floppy disks, tape drives, etc. Therefore, in general, it should be appreciated that system control files may comprise various types of data storage or memory elements having various compositions without departing from the scope of the present invention. Moreover, the access configuration data, parameters, and control settings from the configuration management system 54 may be stored on the various types of data storage or memory elements so as to provide system control files 56 to the operational and treatment devices 11, 12, 14, 18, 20 of the PBTS 10.

Once the configuration data, parameters, etc. are identified and retrieved from the system control file 56, the PBTS control system 62 or the functional components 11, 12, 14, 18, 20 of the PBTS 10 may use the retrieved data, parameters, etc. to configure its functional and operational components for delivery of treatment. It should be appreciated that the PBTS 10 may receive and interpret the PBTS system control files 56 as read-only formatted files that may comprise spreadsheets, tables, etc.

Additionally, the retrieved information may also comprise a set of instructions that may be used by the PBTS 10 to configure its operational components. Advantageously, configuration may occur without depending on the processing and management components of the configuration management system 54 during delivery of treatment. Therefore, the operational components of the PBTS 10 may function in an independent manner, which reduces the adverse effects of single point failures in the configuration management system 54. The management of data, parameters, and control settings by the configuration management system 54 allows for preserving data integrity as well as insuring no duplication of data. For example, data integrity may be preserved with automatic backup, wherein the configuration management system 54 archives backup files comprising copied configuration data, parameters, etc. in a separate storage component without consent from a user. In addition, controlled access to configuration data, parameters, etc. allows the configuration management system 54 to prioritize multiple updates according pre-determined criteria so as to substantially avoid the duplication of configuration data, parameters, etc. Moreover, the PBTS 10 accesses the data, parameters, and control settings from the system control files 56, which insures that the configuration data, parameters, etc. are accessible when and if a single point failures occurs with respect to the configuration management system 54.

For example, configuration of the PBTS 10 may include setting proton energy source 11, the accelerator 12, and the beam transport 14 to deliver a prescribed proton beam 58 to the switchyard 16. In addition, configuration of the PBTS 10 may also include setting the switchyard 16 to direct the prescribed proton beam 60 to a specific treatment station and the corresponding gantry 18 to orient the proton beam 60 towards a specific isocenter 60 on the patient 24. Moreover, configuration data, parameters, etc. may further include length of treatment delivery, energy strength of the proton beam, duration of radiation dosage, and radiating multiple treatment areas on the patient. It is critical to patient safety that the configuration data, parameters, etc. stored in the system control files 56 is locally accessible so that, if the configuration management system 54 goes off line for some reason, the PBTS 10 and its components may remain functional. Advantageously, generation and distribution of system control files 56 to the PBTS treatments delivery system 10 and its components by the configuration management system 54 offers control separation so that the PBTS 10 and its components rely less on the configuration management system 54 to deliver treatments to patients.

In general, it should be appreciated that the PBTS control system 62 and the processing components of the configuration management system 54 may comprise, by way of example, computers, program logic, or other substrate configurations representing data and instructions, which operate as described herein. In various other embodiments, the PBTS control system 58 and the processing and management components of the configuration management system 54 may comprise controller circuitry, processor circuitry, processors, general purpose single-chip or multi-chip microprocessors, digital signal processors, embedded microprocessors, microcontrollers and the like. Additionally, it will be appreciated that in one embodiment, the program logic may be implemented as one or more components, wherein the components may be configured to execute on one or more processors. The components may include, but are not limited to, software or hardware components, modules such as software modules, object-oriented software components, class components and task components, processes methods, functions, attributes, procedures, subroutines, segments of program code, drivers, firmware, micro-code, circuitry, data, databases, data structures, tables, arrays, and variables.

In one aspect, the configuration management system 54 may be implemented using applications designed for relational database development and implementation. It is further recognized that the configuration management system 54 may be implemented as spreadsheet or a single database with separate tables or as other data structures that are well known in the art such as linked lists, binary trees, and so forth. Also, the configuration management system 54 may be implemented as a plurality of databases which are collectively administered. It should also be appreciated that the structure and schema of the configuration management system 54 may be altered, as needed, to implement the relations or associations utilized to organize and categorize the information in the configuration management system 54.

Figure 3A:
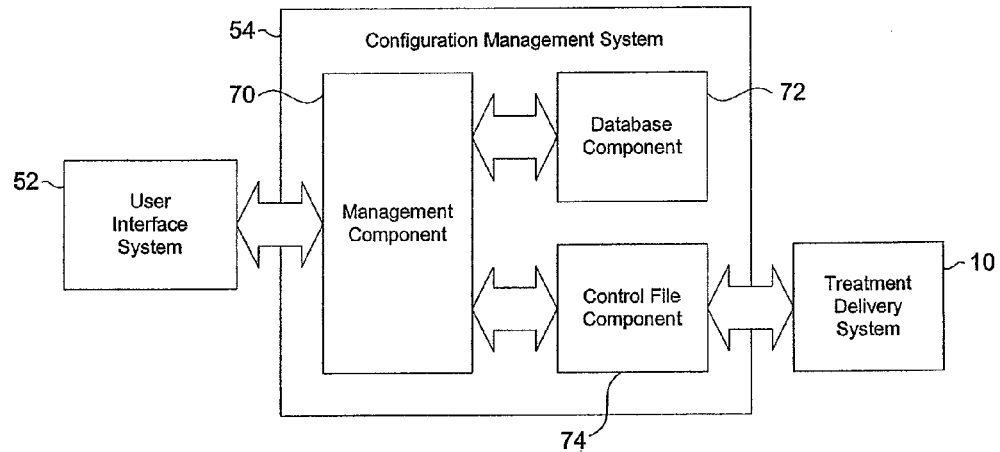
FIG. 3A illustrates a simplified block diagram of the PBTS treatment delivery system, the PBTS user interface system, and the PBTS configuration management system having a management component, a database component, and a control file component.
Figure 3B:
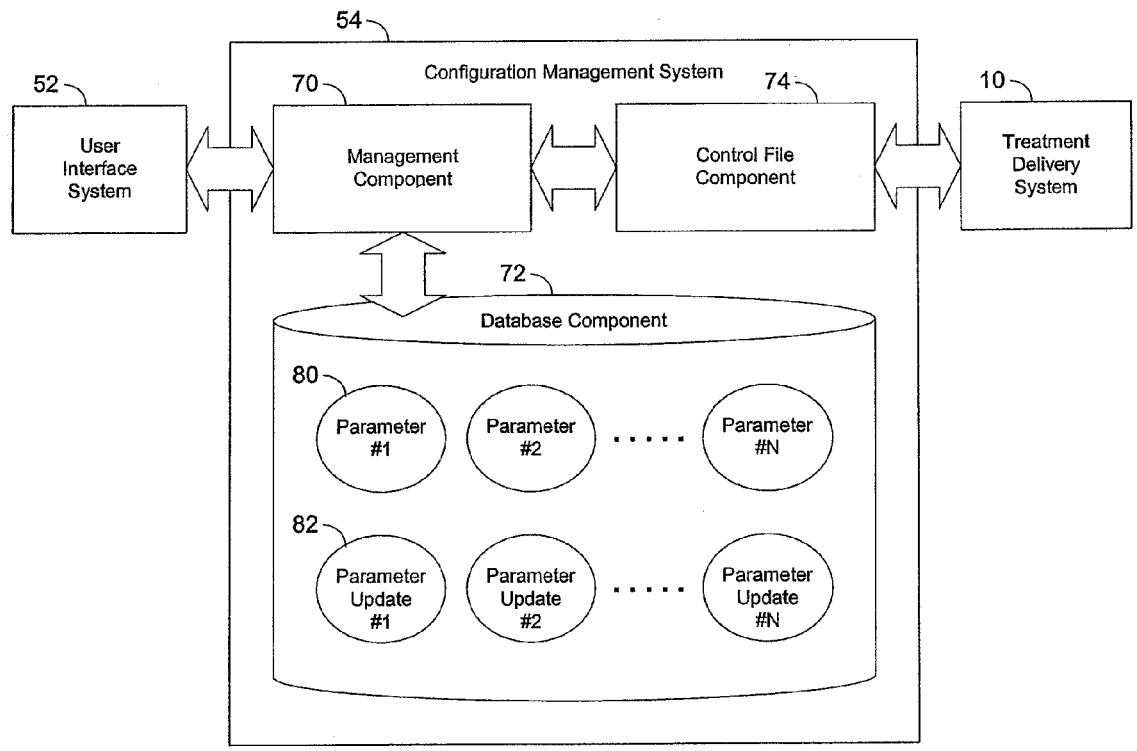
FIG. 3B further illustrates the PBTS configuration management system with functional features associated with the database component.
Figure 3C:
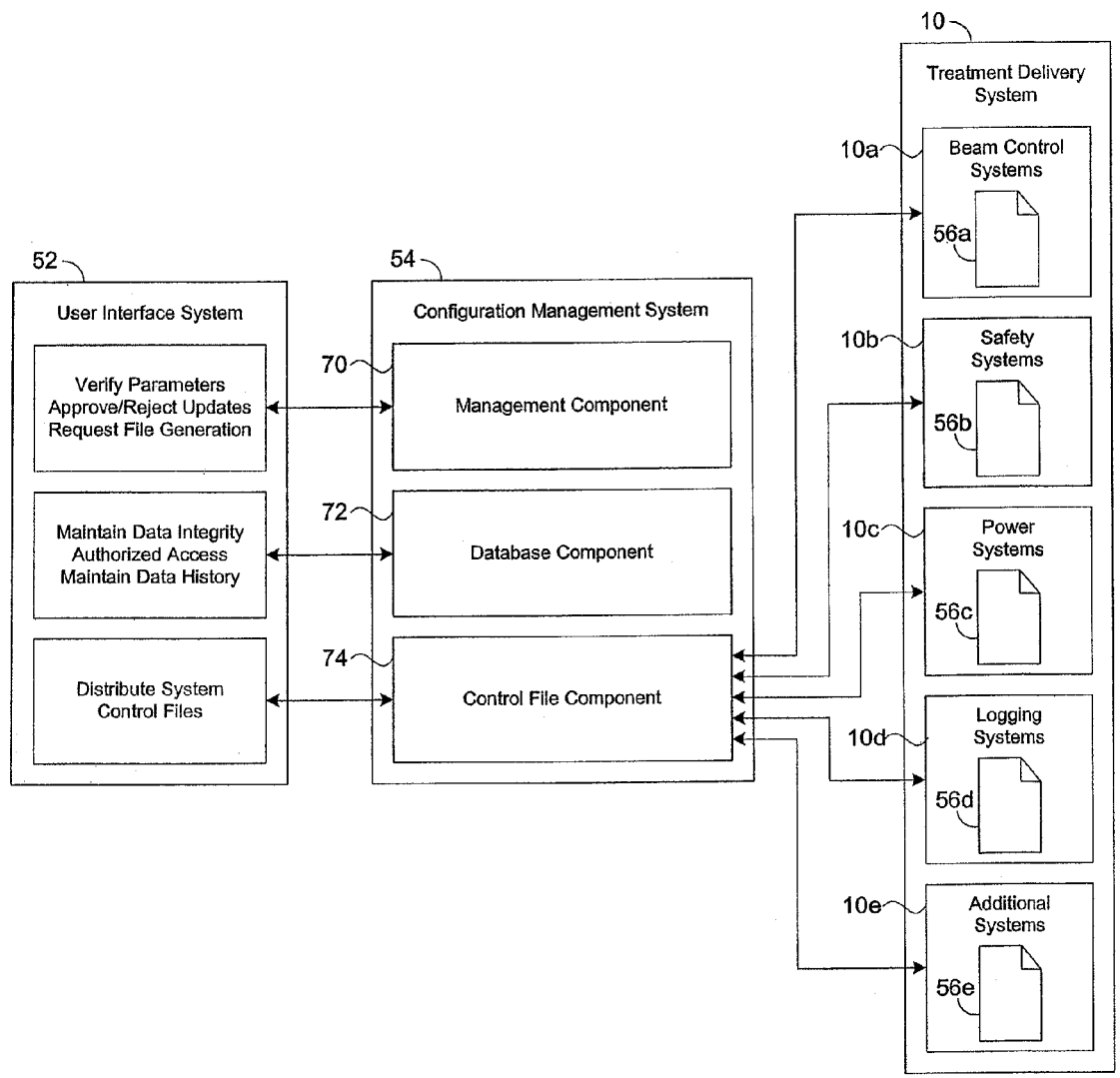
FIG. 3C further illustrates the management component, which may be used by the PBTS configuration management system to identify, retrieve, and update configuration parameters from the database component and to generate system control files using the control file component.

FIGS. 3A-3C illustrate various functional embodiments of the PBTS 10 of FIGS. 1, 2 and the configuration management system 54 of FIG. 2. For ease of discussion, FIG. 3A illustrates a simplified block diagram of the user interface system 52, the configuration management system 54, and the treatment delivery system 10. In this particular embodiment, the configuration management system 54 may comprise a management component 70, a database component 72, and a control file component 74 that are functionally interconnected so as to manage, update, and distribute PBTS configuration data, parameters, and control settings for the PBTS 10. The PBTS database system components 70, 72, 74 may comprise hardware and/or software subsystems that may be adapted for specific functionality with respect to the PBTS 10.

Advantageously, the use of system control files as described herein reduces the occurrence of single point failures by generating a static document, such as, for example, a flat file, binary file, flash memory file, etc., comprising operational and configuration parameters and then distributing the static document to the treatment delivery components. In addition, the distribution of system control files allows the treatment delivery components operational independence from the database component due to the associated reliance on the system control files for operation and parameter retrieval. In one aspect, although a communication link may be used to distribute the generated system control file or static document to one or more of the treatment delivery components, operational reliance may be shifted to the distributed system control file or static document.

For ease of updating and retrieval, configuration parameters, for example, may be stored in the database table structures as records or values. When generating the static document or control file, the retrieved configuration parameter values may be arranged in a consolidated information set that is recognizable by the treatment delivery components. Advantageously, the consolidated information set exploits the native functionality of the treatment delivery devices in a manner such that an additional numerical or supplemental program or application is unnecessary for the treatment delivery devices to parse the configuration parameter values from the static document. The scope and functionality of these processes will be more fully described in greater detail herein below.

In one embodiment, when parameter modifications have been requested, the treatment delivery system 10 receives periodic parameter updates in the form of electronic control files from the configuration management system 54 via, for example, a communication network, such as an Ethernet, intranet, or internet communication system. In some circumstances, the treatment delivery components may send request to the configuration management system inquiring whether parameter updates are available. As will be in greater detail below, the parameter updates are sent to the treatment delivery system in a recognizable format that is easily identified by the treatment delivery components of the system.

FIG. 3B further illustrates the configuration management system 54 of FIGS. 2, 3A with additional functional features associated with the database component 72. Configuration and operational parameters 80, such as data, information, and control settings, may be stored in the database component 72 of the configuration management system 54 as database files in a generally known manner. For example, each PBTS treatment delivery component 11, 12, 14, 16, 18, 20 of the PBTS 10 may have its own set of parameters 80 related to configuration and operation. A relational association may be established in the database component 72 between the particular PBTS treatment delivery component 11, 12, 14, 16, 18, 20 and its own set of parameters 80 from 1 to N. These parameters 80 may be searched for, retrieved, sorted, and edited by the management component 70 in a generally known manner so as to produce parameter update files 82 whenever an authorized user requests a parameter update via the user interface system 52. The process of updating parameters will be described in greater detail herein below.

In one embodiment, the configuration data and parameters are maintained in sets. The database component 72 is responsible for maintaining approved, current, and proposed sets of configuration data and parameters. An approved set may comprise the set of parameter configurations that are acceptable for allowing treatments to proceed. Preferably, for safety reasons, there is only one approved set of configuration parameters at any one time. A current set may comprise the set of parameter configurations that the PBTS 10 is currently being configured with, which may or may not be permissible for treatments. The current set may be one of a plurality of configuration sets stored in the database component 72. A proposed set may comprise a set of parameter configurations waiting approval from a system administrator before it can be used for treatments.

As illustrated in FIG. 3C, the management component 70 may be used by the configuration management system 54 to identify, retrieve, and update configuration parameters from the database component 72 and to generate system control files 56 using the control file component 74. After generating the system control files 56, the management component 70 subsequently distributes the system control files 56*a*, 56*b*, 56*c*, 56*d*, 56*e* to the corresponding PBTS treatment delivery systems 10*a*, 10*b*, 10*c*, 10*d*, 10*e* of the PBTS 10, which may include beam control systems 10*a*, safety systems 10*b*, power systems 10*c*, logging systems 10*d*, and various additional systems 10*e*. Beam control systems 10*a* may include the beam transport 14, the switchyard, the gantry 18 and the beam delivery system 20. Power systems 10*c* may include the proton energy source 11 and the accelerator 12.

The database component 72 may function in the capacity of generally known memory devices, such as hard drives, compact discs, removable storage media, tape drives, flash memory, optical devices, integrated circuitry, etc., wherein the parameter information may easily stored, altered, and retrieved by the user interface system 52. The control file component 74 may function as relational translator that interprets database language formats into control file language formats so that configuration parameters stored in the database may translated into recognizable operational parameters for the functional components of the PBTS 10.

In a complex, multi-processor software controlled system, such as the PBTS 10, it may be important to provide treatment configurable parameters that are easily modified by an authorized user to prepare the software controlled system for various modes of operation, such as modifying parameter tolerance, user access, access levels, debug output, etc. In most cases, configuration parameters are loaded by execution software of the PBTS 10 in a safe and timely manner. Moreover, the PBTS 10 often involves multiple modes of operation (treatment, research, commissioning), multiple configuration setups (passive beam delivery, active beam delivery), and multiple patient setups. In addition, there may be more than one person who has authorized access to modify data and parameter sets.

In one embodiment, the configuration management system 54 provides a centralized database server, which stores configuration and operational information, such as data, parameters, and control settings, for the software controlled PBTS 10. In one embodiment, parameter modification and parameter retrieval are performed by the configuration management system 54 via requests from the user interface system 52. Moreover, the configuration management system 54 provides configuration management activities, which may include record keeping (i.e., who, when, and why modified certain parameter, has a parameter been approved for a certain mode), providing backup of the data, and version/revision control. Additionally, configuration data and parameters may be temporarily changed in a manner such that, after a designated time period, newly modified values of configuration data and parameters may revert back to previously stored values. Reversion to previous data, parameters, etc. may also occur after the system control files 56 are generated.

In one aspect, modifying data and parameters may be subject to approval by an administrator, which helps to maintain data integrity and insure proper treatment dosages and delivery. The system administrator may either approve, reject, or institute a time limit for the modification availability. In some cases, if duplicate modification requests are requested by one or more authorized users and the system administrator approves all pending modification requests, then the latest modification request may override all other requests. In other cases, a time out period indicates that the system administrator is approving a proposed modification but only for a limited amount of time. In this particular situation, once the specified date and/or time have elapsed, the previous value of the data or parameter prior to the modification request will be reinstated.

Advantageously, the configuration management system 54 comprises the capability to generate system control files 56 to substantially avoid problematic situations that may occur during operation of the PBTS 10. Network problems and single-point failures may occur as the result of an unexpected shutdown and/or an emergence of a corrupted file. The system control files 56 may comprise various types of control files, such as, for example, flat files, binary files, flash memory files, etc., that provide fast, localized parameter retrieval capability and independent operational capabilities for the PBTS 10. In one aspect, modifying configuration data and parameters during treatments may adversely affect the treatment delivery. Therefore, for safety reasons, system control files 56 are preferably generated between treatments.

Additionally, the configuration management system 54 comprises an information management and retrieval system with adequate configuration management capabilities and fast, safe, and localized parameter retrieval. For example, the configuration management system 54 utilizes the management component 70 in conjunction with the database component 72 to provide restricted access to parameter modification, wherein authorized users are allowed to revise configuration data, parameters, etc. and unauthorized users are not granted access to the configuration data, parameters, etc. In addition, the configuration management system 54 uses the management component 70 in conjunction with the control file component 74 to generate the system control files 56 from parameter files 80, 82 for distribution of configuration parameters to the PBTS 10.

In one aspect, on a periodic basis or when a parameter has been modified either temporarily or permanently, the configuration management system 54 may generate system control files 56 from the parameter files 80, 82, substantially insuring that proper syntax has been followed during generation. For example, the management component 70 has access to the programming language used by each of the treatment delivery components in the PBTS 10. In one aspect, proper syntax may comprise using a specific set of rules prescribed by the programming language to combine instructional elements into permitted constructions that will be recognizable to the designated treatment delivery component. Proper syntax may also refer to a systematic arrangement of data and instructions that may be easily parsed from the system control files 56 by the designated treatment delivery component. Moreover, the generated system control files 56 are then placed in the appropriate directories associated with the functional components of the PBTS 10. In addition, execution software used by the functional components of the PBTS 10 retrieves the appropriate system control file 56 and loads the requested configuration parameters for treatment delivery.

Figure 4A:
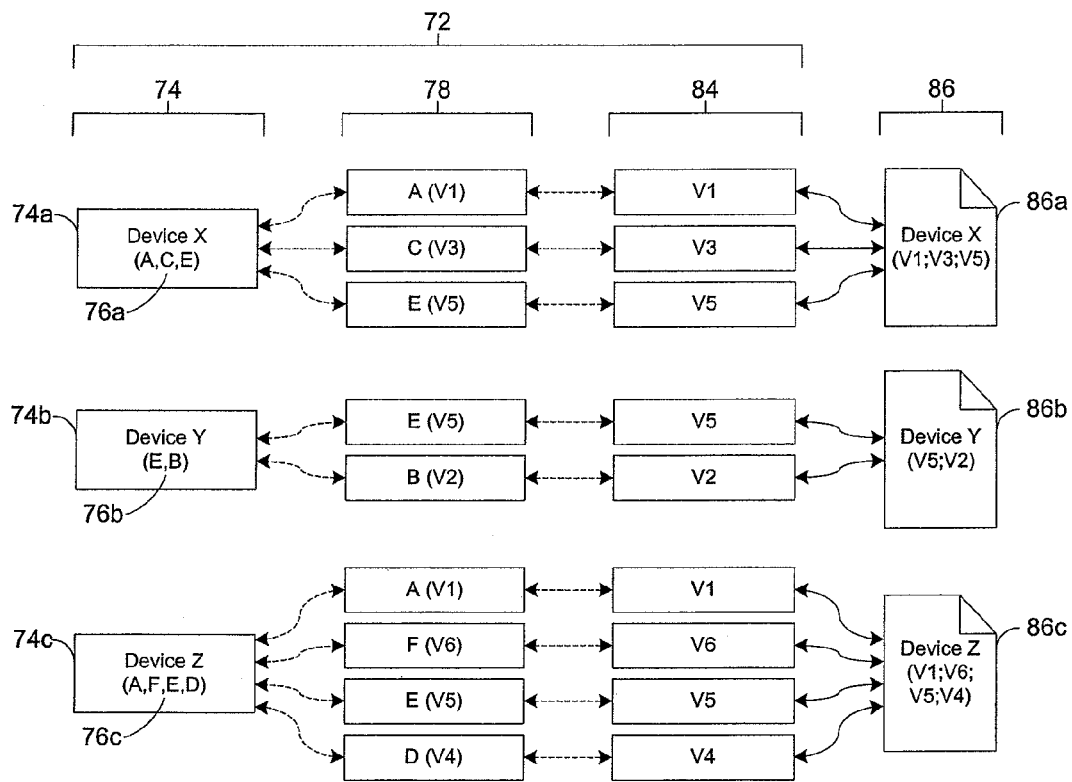
FIG. 4A illustrates one embodiment of a logical organization of the configuration parameters in the database component.

FIG. 4A illustrates one embodiment of a logical organization of a plurality of configuration parameter values 80 in the database component 72. As previously described, there are a significant number of configuration parameter values 80 that may be applied to each PBTS treatment delivery component in the PBTS 10. Tracking the configuration parameter values for PBTS treatment delivery components can be highly complex and cumbersome. Therefore, the management component 70 may be used to map parameters to specific treatment delivery components in the PBTS 10 using a plurality of mapping tables 74. In the database component 72, the mapping tables 74 comprising deployment labels 76a, 76b, 76c to lookup keys 78 may be created to identify and retrieve configuration parameter values 80 to thereby generate a plurality of system control files 86. In one aspect, the lookup keys 78 identify where the data and parameter values 80 can be located within the database component 72, wherein each deployment label 76 points to a specific lookup key 78 where the data or parameter values 80 can be found in the database component 72.

For example, a first treatment delivery component of the PBTS 10 may be mapped to a first mapping table 74a comprising a first set of deployment labels 76a. A second treatment delivery component of the PBTS 10 may be mapped to a second mapping table 74b comprising a second set of deployment labels 76b. A third treatment delivery component of the PBTS 10 may be mapped to a third mapping table 74c comprising a third set of deployment labels 76c. As illustrated in FIG. 4A, the first set of deployment labels 76a may point to lookup keys A, C, and E, (78) which may further point to configuration parameter values V1, V2, and V5 (80). The second set of deployment labels 76b may point to lookup keys B and E (78), which may further point to configuration parameter values V2 and V5 (80). The third set of deployment labels 76c may point to lookup keys A, D, E, and F (78), which may further point to configuration parameter values V1, V4, V5, and V6 (80).

For the most part, parameter referencing, as indicated in FIG. 4A with a dashed line, takes place in the database component 72 in a generally known manner. In one aspect, once the configuration parameter values 80 have been identified and retrieved, the configuration parameter values 80 may be subsequently imported, as illustrated in FIG. 4A with a solid line, into the system control files 86 for distribution to the corresponding PBTS treatment delivery component in the PBTS 10. For example, the first mapping table 74a may be used to generate and distribute a first system control file 86a to the first treatment delivery component of the PBTS 10. The second mapping table 74b may be used to generate and distribute a second system control file 86b to the second treatment delivery component of the PBTS 10. The third mapping table 74c may be used to generate and distribute a third system control file 86c to the third treatment delivery component of the PBTS 10.

It should be appreciated that the order in which the parameter values are retrieved may vary and may depend on the specific order in which the designated treatment delivery component parses the information from the control file. It should also be appreciated that any number of control file generation techniques may be used by one skilled in the art without departing from the scope of the present invention.

As previously described, treatment parameter values may need to be updated to reflect new treatment dosages, etc. Therefore, once the configuration parameter values 80 have been identified and located in the database component 72, the configuration parameters values 80 may be replaced or revised with updated configuration parameters values 82. It should be appreciated that storing data and information is generally known in the art and any of a number of generally known storage methods may be used to store the updated configuration parameters values 80 in the database component 72.

Figure 4B:
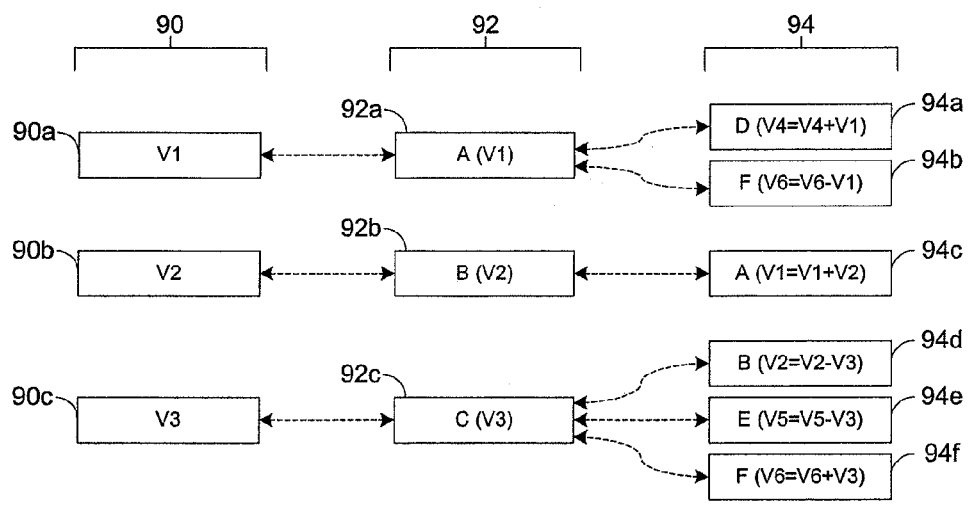
FIG. 4B illustrates one embodiment of configuration parameter associations, wherein modifications to one parameter may effect other parameters.

FIG. 4B illustrates one embodiment of a logical organization of configuration parameter associations 94. User input modifications 90 to specific configuration parameters may effect other dependent configuration parameters in a manner such that the dependent configuration parameter values may need to be re-calculated. In one aspect, a plurality referential locations 92 may be used to identify a plurality of parameter associations 94 corresponding to the user inputted modifications 90. For example, as illustrated in FIG. 4B, a first input modification 90a to a first configuration parameter value V1 referenced by lookup key A may point to a first referential location 92a, which may further point to a first and second parameter association 94a, 94b. Since V1 has been modified by the user, the database component 72 locates the configuration parameter values V4 and V6 associated with the lookup keys D and F. Subsequently, the configuration parameter values V4 and V6 may then be re-calculated according to a specified function, such as V4=V4+V1 and V6=V6+V1. It should be appreciated that the re-calculation function may vary depending on a particular application without departing from the scope of the present invention.

Similarly, in another example, a second input modification 90a to a second configuration parameter value V2 referenced by lookup key B may point to a second referential location 92b, which may further point to a third parameter association 94c. Since V2 has been modified by the user, the database component 72 locates the configuration parameter value V1 associated with the lookup key A. Subsequently, the configuration parameter value V1 may then be re-calculated according to a specified function, such as V1=V1+V2. In addition, a third input modification 90c to a third configuration parameter value V3 referenced by lookup key C may point to a third referential location 92c, which may further point to a fourth, fifth, and sixth parameter association 94d, 94e, 94f. Since V3 has been modified by the user, the database component 72 locates the configuration parameter values V2, V5, and V6 associated with the lookup keys B, E, and F. Subsequently, the configuration parameter values V2, V5, and V6 may then be re-calculated according to a specified function, such as V2=V2+V3, V5=V5+V3, and V6=V6+V3.

It should be appreciated that the order in which the configuration parameter values are re-calculated may vary depending on specific application priorities established by the user. As previously mentioned, the most recent modification may be given priority over past modifications or priority may be established by a configuration administrator. It should also be appreciated that any number of parameter association techniques may be used by one skilled in the art without departing from the scope of the present invention.

Figure 4C:
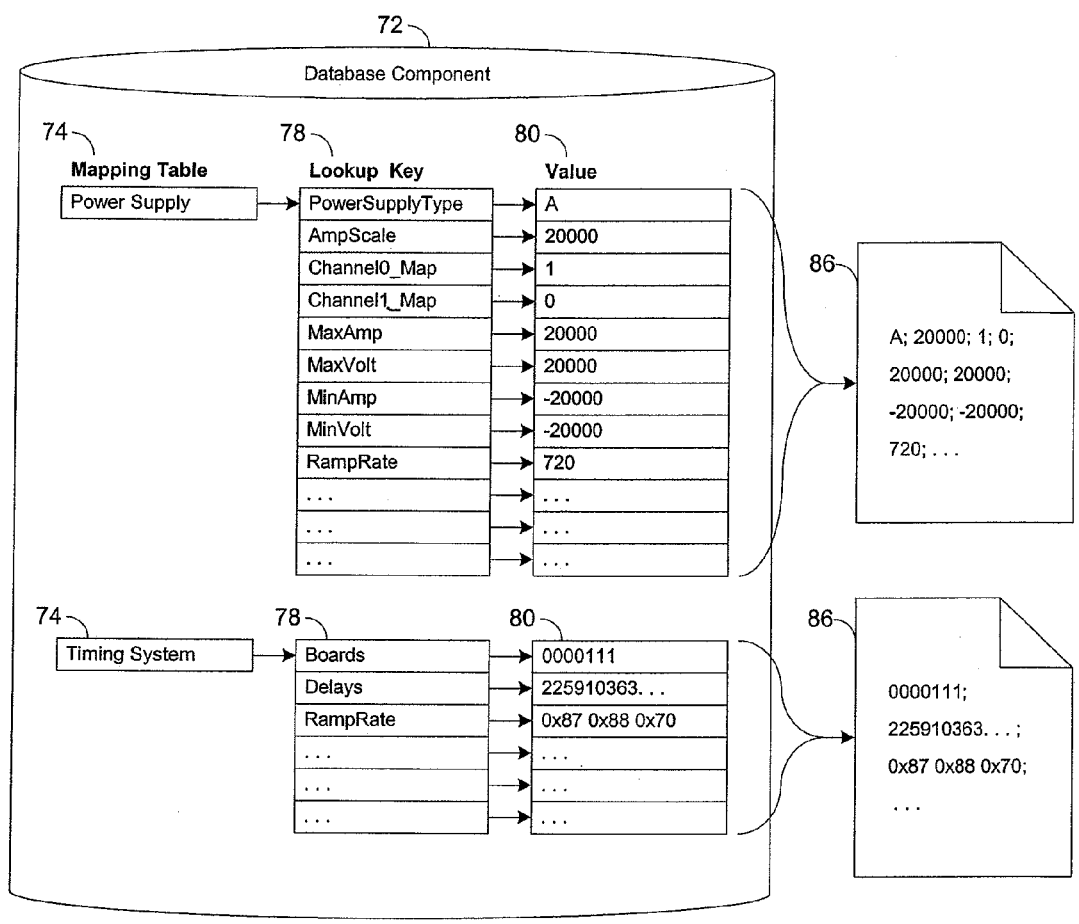
FIG. 4C illustrates one example of using mapping tables to generate system control files associated with specific treatment delivery devices in the PBTS.

FIG. 4C illustrates one example of using mapping tables 74 to generate system control files 86 associated with specific treatment delivery devices in the PBTS 10. In one embodiment, the mapping tables 74 comprise records and keys for maintaining the data as well as the actual parameters and their associated attributes. As previously described, the configuration management system 54 uses input data from authorized users via the user interface device 52 to manipulate or modify the configuration data, parameters, etc. in the database component 72. This data is made available to the treatment delivery components and devices in the PBTS 10 as a mapping from the tables to text based control files 86. For example, the power supply in the PBTS 10 may be used to energize one or more magnets in order to reach the desired energy and control the beam in a generally known manner. There are different types of power supplies and each type of power supply may be configured differently. As a result, the configuration parameters associated with the power supplies may be stored in the database component 72.

As illustrated in FIG. 4C, the configuration parameters may be stored, for example, in the database component 72 using tables. In one aspect, the tables hold information that is used to look up and maintain the parameters and their values in a manner as previously described with reference to FIGS. 4A, 4B and as illustrated herein below.

| | | | | | | | |
|---|---|---|---|---|---|---|---|
| ... | ... | ... | ... ... | ... | | ... | ... ... ... |
| ... | ... | ... | ... ... | ... | | ... | ... ... ... |
| attr1 | attr2 | ... | ... ... | AmpScale | 20000 | ... | ... attrn |
| attr1 | attr2 | ... | ... ... | MaxAmp | 20000 | ... | ... attrn |
| attr1 | attr2 | ... | ... ... | MaxVolt | 20000 | ... | ... attrn |
| attr1 | attr2 | ... | ... ... | MinAmp | −20000 | ... | ... attrn |
| attr1 | attr2 | ... | ... ... | MinVolt | −20000 | ... | ... attrn |
| attr1 | attr2 | ... | ... ... | RampRate | 720 | ... | ... attrn |
| ... | ... | ... | ... ... | ... | | ... | ... ... ... |
| ... | ... | ... | ... ... | ... | | ... | ... ... ... |

-continued

| | | | | | | |
|---|---|---|---|---|---|---|
| ... | ... | ... | ... ... | ... | ... | ... ... ... |
| ... | ... | ... | ... ... | ... | ... | ... ... ... |
| ... | ... | ... | ... ... | ... | ... | ... ... ... |
| ... | ... | ... | ... ... | ... | ... | ... ... ... |

In one embodiment, the management component 70 of the configuration management system 54 uses the database component 72 to select necessary parameter values 80 and further uses the control file component 74 to write the parameter values 80 to control files 86. As a result, the configuration parameter values in control file form 86 are available for retrieval by the designated treatment delivery components of the PBTS 10.

For example, as illustrated in FIG. 4C, the database component 72 may comprise a mapping table 74 for the power supply. The power supply mapping table 74 comprises deployment labels that point to one or more lookup keys 78 which further point to configuration parameter values 80 associated with the power supply. These configuration parameter values 80 for the power supply may be imported into a control file 86 for distribution to the power supply component of the PBTS 10. In another example, as illustrated in FIG. 4C, the database component 72 may further comprise a mapping table 74 for a timing system. The timing system mapping table 74 comprises deployment labels that point to one or more lookup keys 78 which further point to configuration parameter values 80 associated with the timing system. These configuration parameter values 80 for the timing system may be imported into a control file 86 for distribution to the timing system component of the PBTS 10.

Figure 5:
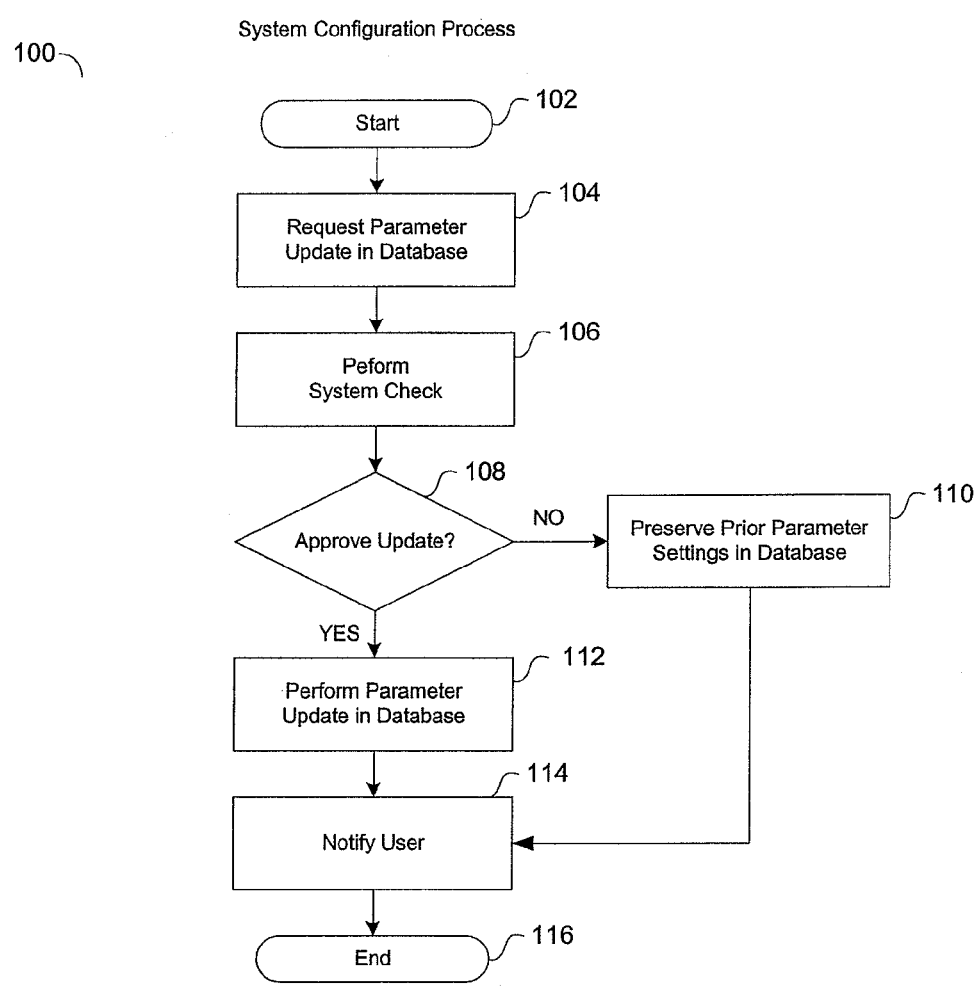
FIG. 5 illustrates one embodiment of a system configuration process that may be used by the PBTS configuration management system to modify parameters for the PBTS treatment delivery system.

FIG. 5 illustrates one embodiment of a system configuration process 100 that may be used by the configuration management system 54 to modify parameters for the PBTS 10. The database component 72 of the PBTS configuration management component 54 is used to maintain and preserve the integrity of configuration data, parameters, etc. in a manner so as to avoid duplicating configuration settings. In addition, the stored configuration data, parameters, etc. may be easily retrieved, modified, and archived so that configuration parameters may be updated in a more efficient manner.

The system configuration process 100 initiates in a start state 102 and then advances to a state 104 where a user may request a parameter update via the user interface system 52. In one embodiment, the user enters new system configuration parameters into the user interface system 52 via a computer workstation, and the requested parameter update having the new system configuration parameters is electronically sent to the configuration management system 54 for evaluation. Subsequently, upon receiving the requested parameter update, the management component 70 of the configuration management system 54 runs through a PBTS system check that compares the new system configuration parameters to a tolerance range of values. For example, if the operational range of a power supply is between 0 and 500 amps, then the management component 70 verifies that the new system configuration parameter for the power supply is not set less than 0 amps and greater than 500 amps.

In a decision state 108, if one or more of the new system configuration parameters in the requested parameter update are out of tolerance range, then the prior database settings for the prior system configuration parameters are preserved and the user is notified in a state 114 and the process 100 subsequently terminates in an end state 116. Otherwise, in the decision state 108, if the new configuration parameters in the requested parameter update fall with the pre-determined tolerance ranges then the process 100 proceeds to a state 112 where the management component 70 of the configuration management system 54 performs a parameter update as described in greater detail herein below with reference to FIG. 6. Once the system configuration parameters in the database component 72 of the configuration management system 54 have been updated to the new system configuration parameters in the requested parameter update, the user is notified in the state 114, and the process 100 terminates in the end state 116.

As previously described, in a complex, multi-processor software controlled system, such as the PBTS 10, it may be important to provide treatment configurable parameters that are easily modified by an authorized user to prepare the software controlled system for various modes of operation. Advantageously, the configuration management system 54 provides a centralized database, which efficiently stores configuration data, parameters, etc., for the software controlled PBTS 10. Also, parameter modification and parameter retrieval may be efficiently performed by the configuration management system 54 via requests from the user interface system 52.

Figure 6:
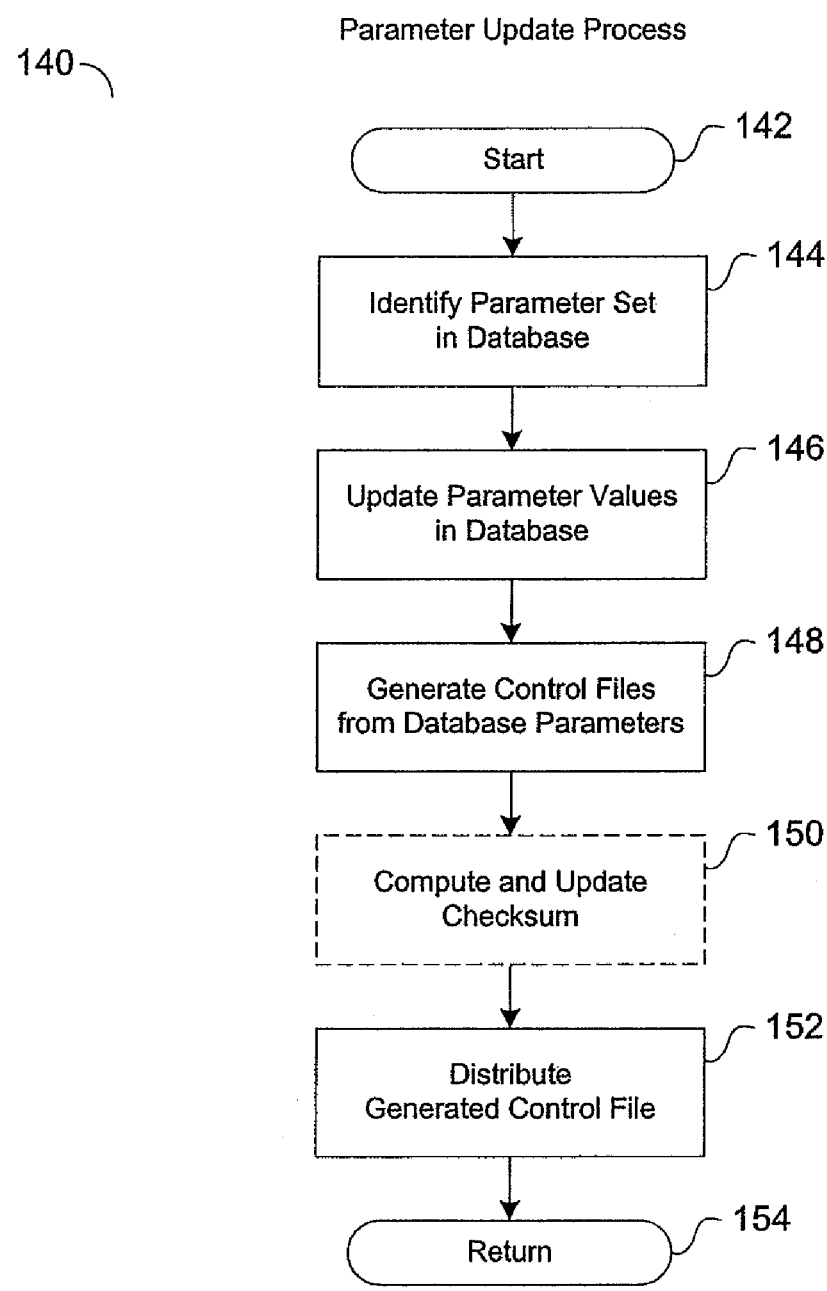
FIG. 6 illustrates one embodiment of a parameter update process that may be used by the management component of the PBTS configuration management system to update system configuration parameters used by the PBTS treatment delivery system.

FIG. 6 illustrates one embodiment of a parameter update process 140 that may be used by the management component 70 of the configuration management system 54 to update system configuration parameters used by the PBTS 10. The updated parameters are easily identified and retrieved from the database files and then converted to control files for distribution to the PBTS 10. Generation and distribution of system control files 56 to the PBTS treatments delivery system 10 and its components by the configuration management system 54 offers control separation so that the PBTS 10 and its components rely less on the configuration management system 54 to deliver treatments to patients. For ease of discussion, FIG. 3B will be referenced in conjunction with FIG. 6.

The parameter update process 140 initiates in a start state 142 and proceeds to a state 144 where the management component 70 of the configuration management system 54 identifies the parameters 80 associated with the requested parameter update 82 in the database component 72. In a state 146, the new system configuration parameters in the requested parameter update 82 are temporarily stored in the database component of the configuration management system 54 while waiting approval from a system administrator.

After modification approval is granted, either the requested parameter update 82 is stored in a permanent manner so as to replace the previous parameters 80 with the parameter update 82, or the requested parameter update 82 is used to generate system control files 56 for a specific treatment and the previous parameters 80 are maintained in the database component 72. By temporarily storing the parameter update 82, duplication of data does not occur, and the previous parameters 80 are not lost. A temporary parameter update 82 will have a specified time period for expiration in a manner as previously described. This allows for increased treatment flexibility in that treatment dosages can vary for each treatment delivery without losing prior configuration parameters.

Next, in a state 148, the management component 70 uses the control file component 74 to generate the system control file 56 with the new system configuration parameters from the requested parameter update 82. In one embodiment, the management component 70 retrieves configuration parameters from the database component 72 and queues the parameter values in a string by separating each value with a delimiter. In one aspect, the control file component 74 has prior knowledge of the order in which the parameter values will be parsed by the designated functional component of the PBTS 10. Hence, the management component 70 uses the control file component 74 to track the placement of each parameter value in the queue so that the system control file 56 will be appropriately generated with the correct parsing order.

Optionally, the management component 70 may then calculate and update the checksum, which checks the generated system control file 56 for errors. In one aspect, generated system control files 56 provide checksum mechanisms to verify that generated data is current and up-to-date. When the system control files 56 are generated, the management component 70 uses a checksum algorithm to allow the detection of file corruption. The checksum method is a common form of detecting corruption in network transfer of data packets. The sending process appends a checksum to the end of the packet that the receiver uses to confirm the packet is not corrupted. There are many checksum algorithms out there. They basically take the information in the packet/file and perform mathematical operations and/or logical operations (bit shifting, bit twiddling, etc.) to "sum" the packet/file. The receiving process uses the same algorithm on the data and compares it to the checksum. If they match, there is no data corruption. Following, the configuration management system 54 establishes communication with PBTS 10 and distributes the generated system control file 56 to the appropriate functional component of the PBTS 10. Subsequently, the parameter update process 140 terminates in an end state 154.

Advantageously, the PBTS 10 or its operational components accesses the data, parameters, etc. through the system control files 56. This substantially insures that the data, parameter, etc. may be accessible even when and if a single point failures occurs with respect to the configuration management system 54. In addition, configuration of the PBTS 10 or its operational components may be achieved without depending on the configuration management system 54 during treatment delivery. Therefore, the PBTS 10 and its operational components may function in an independent manner, which reduces the adverse effects of single point failures in the configuration management system 54.

Figure 7:
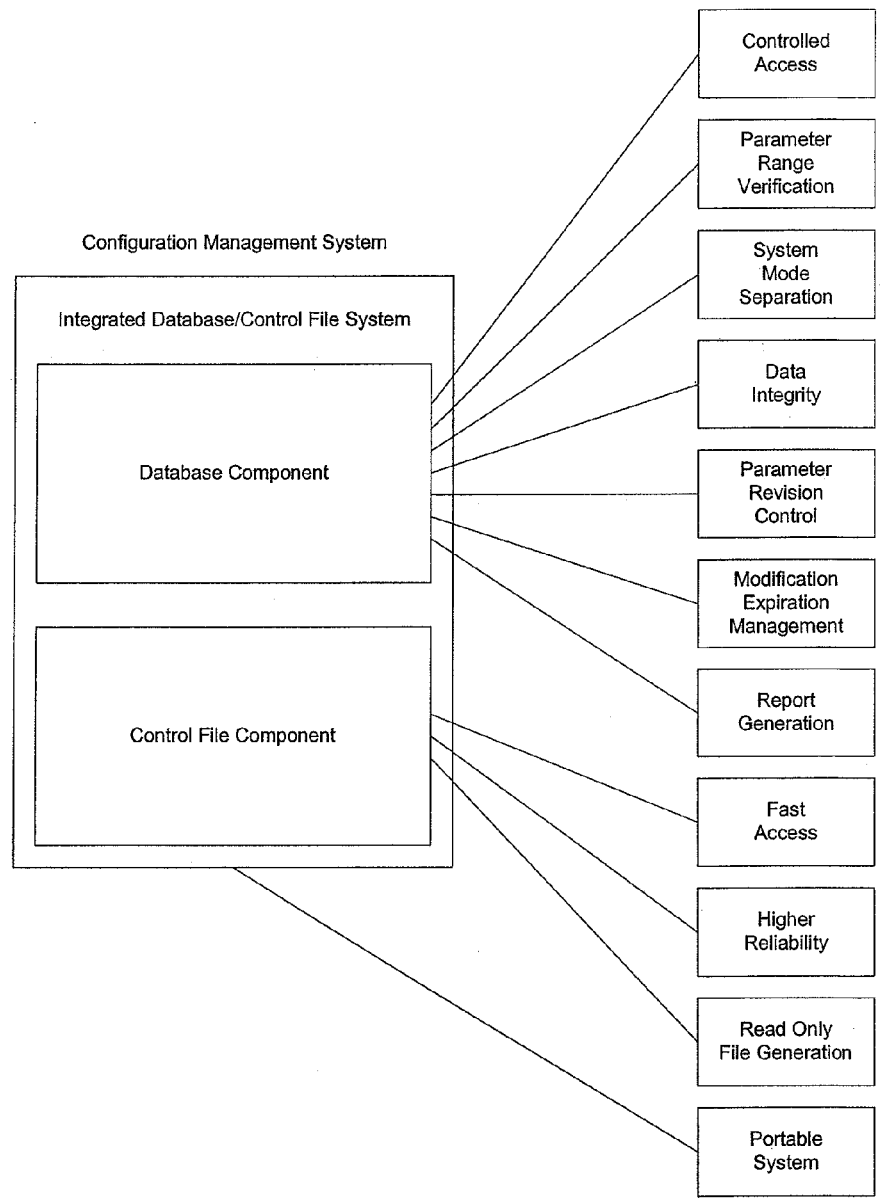
FIG. 7 illustrates the advantages of using the PBTS configuration management system of the present invention to manage, update, and distribute configuration parameters for the PBTS treatment delivery system.

FIG. 7 illustrates the advantages of using the configuration management system 54 of the present invention to manage, update, and distribute configuration parameters for the PBTS 10. Advantageously, the configuration management system 54, as described herein, utilizes the positive characteristics of both database oriented file management systems and control files configuration systems.

As illustrated in FIG. 7, with reference to the database management systems, the configuration management system 54 provides controlled access to configuration information, such as authentication and logging, parameter range verification before parameter is read by the PBTS 10, operational mode separation in configuration parameters, automated backup, and data integrity. In addition, the database management system may further provide revision control for a single parameter, parameter modification expiration date management, and report generation capabilities to insure the proper syntax, data integrity of the system control files.

As further illustrated in FIG. 7, with reference to the control file configuration systems, the configuration management system 54 provides fast access to configuration parameters in system control files, which may take less time to access a file than accessing a field in the database, and provides localized access to configuration parameters with higher reliability, which substantially insures that parameter information is accessible in case of database server or network interruptions and/or failures. Additionally, the control file configuration system may further provide configuration information in an archived or read-only format to the user, administrator, and/or system operator. It should be appreciated that the configuration management system 54 may be added on or to existing control files configuration systems in various currently used medical devices by one skilled in the art without departing from the scope of the present invention.

Although the preferred embodiment of the present invention has shown, described, and pointed out the fundamental novel features of the invention as applied to this particular embodiment, it will be understood that various omissions, substitutions and changes in the form of the detail of the device illustrated may be made by those skilled in the art without departing from the spirit of the present invention. Consequently, the scope of the invention should not be limited to the foregoing description, but should be defined by the appending claims.

What is claimed is:

1. A radiation beam therapy system comprising:
   an assembly of treatment devices, including:
      a charged-particle accelerator that provides a beam of energetic charged particles;
      a treatment station that allows positioning of a patient to receive at least a portion of the beam of charged particles; and
      a beam delivery system that delivers the beam of charged particles to the patient positioned at the treatment location;
   a database component that stores subsets of parameters associated with selected treatment devices, wherein the parameters comprise instructional information that can be used to configure the selected treatment devices for operation;
   an interface component that allows a user to modify the subsets of parameters associated with selected treatment devices stored in the database wherein the system is configured so that changes to the stored subsets of parameters in the database component can only be made through the interface component; and
   a management component that extracts subsets of parameters from the database and generates data storage elements comprising the extracted subsets of parameters in a format recognizable by the selected treatment devices, wherein the data storage elements permit configuration of the selected treatment devices based, at least in part, on the instructional information comprised therein, the management component further distributes the data storage elements to the selected treatment devices to thereby permit the selected treatment devices to operate independently of the database component.

2. The system of claim 1, wherein the beam of charged particles comprises a beam of protons.

3. The system of claim 2, wherein the treatment station comprises a rotatable gantry that allows delivery of the beam of protons to the positioned patient from a plurality of angles.

4. The system of claim 1, wherein the subsets of parameters include treatment data, configuration parameters, operational parameters, and control settings for the selected treatment devices.

5. The system of claim 4, wherein the selected treatment devices are software controlled instruments that require at least one of the subsets of parameters for operation and treatment.

6. The system of claim 1, wherein the database component comprises a centralized database server, which stores configuration and operational information, such as data, parameters, and control settings, for the selected treatment devices in a manner so as to provide easy access to the stored configuration and operational information, wherein parameter retrieval and modification are easily performed by the centralized database server via requests from the interface component.

7. The system of claim 6, wherein the centralized database server provides configuration management activities, which includes record keeping and version/revision control.

8. The system of claim 1, wherein the interface component only permits changes to the stored parameters during time periods when the management component is not extracting subsets of parameters from the database and distributing such extracted parameters to the selected treatment devices.

9. The system of claim 1, wherein the management component reduces the occurrence of single point failures by generating appropriate data storage elements and distributing the data storage elements to the selected treatment devices.

10. The system of claim 9, wherein the distribution of data storage elements by the management component affords the selected treatment devices operational independence from the database component due to the associated reliance on the data storage elements for parameter retrieval and operational configuration.

11. The system of claim 1, further comprising at least one communication link between the management component and the selected treatment devices so as to distribute the generated data storage elements to the selected treatment devices.

12. The system of claim 1, wherein the subsets of parameters are stored in the database component in at least one of database table structures, records, and values.

13. The system of claim 1, wherein the data storage elements are arranged in a consolidated information set that is recognizable by the selected treatment devices.

14. The system of claim 13, wherein the consolidated information set exploits the native functionality of the selected treatment devices in a manner such that an additional numerical or supplemental program or application is unnecessary for the selected treatment devices to recognize the configuration parameter values from the data storage elements.

15. The system of claim 1, wherein the data storage elements comprise a data type that is stored and accessed in a file-oriented manner as is suitable for each selected treatment devices.

16. The system of claim 1, wherein the data storage elements comprise a data type that is stored and accessed in an address-oriented manner as is suitable for each selected treatment devices.

17. The system of claim 1, wherein the data storage elements comprise one or more volatile or non-volatile system control files.

18. The system of claim 1, wherein the data storage elements comprise one or more system control files.

19. The system of claim 18, wherein the one or more system control files include one or more flat files.

20. The system of claim 1, wherein the management component sends configurable parameters to each treatment device, and wherein a selected treatment device retrieves usable parameters from the configurable parameters.

21. The system of claim 1, wherein the management component selectively sends configurable parameters to each treatment device representing usable parameters by each treatment device.

22. A radiation beam therapy system comprising:
a plurality of distributed functional components that operate to provide a radiation beam to a patient;
a database component that stores a plurality of parameters associated with the distributed functional components,
an interface component that allows a user to select an operational mode for which the database component identifies appropriate subsets of parameters that are associated with the distributed functional components and generates at least one system control file containing an appropriate subset of parameters used to configure a selected distributed functional component to operate in a selected manner wherein the subsets of parameters can only be changed via the interface component; and
a control file distribution component that provides each of the distributed functional components with the appropriate system control file such that the functional components are able to operate substantially independently of the database component to thereby reduce the likelihood of a single point failure of the radiation beam therapy system and wherein changes to the subsets of parameters can only be made when system control files are not being distributed.

23. The system of claim 22, wherein the distributed functional components are software controlled instruments that require at least one of the plurality of parameters for operation.

* * * * *